United States Patent
Paine

(10) Patent No.: US 9,013,313 B2
(45) Date of Patent: Apr. 21, 2015

(54) BED PRE-EXIT PATIENT MONITOR

(76) Inventor: Alan Paine, San Dimas, CA (US)

( * ) Notice: Subject to any disclaimer, the term of this patent is extended or adjusted under 35 U.S.C. 154(b) by 459 days.

(21) Appl. No.: 13/352,278

(22) Filed: Jan. 17, 2012

(65) Prior Publication Data

US 2012/0182148 A1 Jul. 19, 2012

Related U.S. Application Data

(60) Provisional application No. 61/433,754, filed on Jan. 18, 2011.

(51) Int. Cl.
- *G08B 23/00* (2006.01)
- *A61B 5/11* (2006.01)
- *G08B 21/04* (2006.01)

(52) U.S. Cl.
CPC .......... *A61B 5/1115* (2013.01); *G08B 21/0461* (2013.01); *A61B 2560/0223* (2013.01)

(58) Field of Classification Search
CPC .. G08B 21/22; G08B 21/0461; G08B 25/008; G01G 19/021; A61B 5/1115; A61B 2560/0223; G06Q 50/24; G06Q 50/22; A61G 7/018; A61G 2007/0524; A61G 2203/44; A61G 2007/0527
USPC .................. 340/573.4, 8.1, 286.07, 665, 666; 348/77; 600/587; 705/2
See application file for complete search history.

(56) References Cited

U.S. PATENT DOCUMENTS

| | | | |
|---|---|---|---|
| 2,817,477 A | 12/1957 | Gollhofer | |
| 3,781,843 A | 12/1973 | Harrison et al. | |
| RE28,754 E | 3/1976 | Cook et al. | |
| 3,961,201 A | 6/1976 | Rosenthal | |
| 4,020,482 A | 4/1977 | Feldl | |
| 4,242,672 A | 12/1980 | Gault | |
| 4,539,560 A | 9/1985 | Fleck et al. | |
| 4,633,237 A | 12/1986 | Tucknott et al. | |
| 4,692,082 A * | 9/1987 | Smith | 414/429 |
| 4,934,468 A * | 6/1990 | Koerber et al. | 177/144 |
| 5,112,070 A * | 5/1992 | Hahn | 280/79.4 |
| 5,140,309 A * | 8/1992 | Gusakov | 340/573.4 |
| 5,235,319 A | 8/1993 | Hill et al. | |
| 5,276,432 A * | 1/1994 | Travis | 340/573.4 |
| 5,823,278 A | 10/1998 | Geringer | |
| 5,831,221 A | 11/1998 | Geringer | |
| 5,844,488 A | 12/1998 | Musick | |
| 5,861,582 A * | 1/1999 | Flanagan et al. | 177/144 |

(Continued)

*Primary Examiner* — Benjamin Lee
*Assistant Examiner* — Quang D Pham
(74) *Attorney, Agent, or Firm* — Kirk A. Buhler; Buhler & Associates

(57) ABSTRACT

Improvements in a bed pre exit patient monitor to determine when a patient has moved to an edge of a bed prior to the patient leaving the bed by measuring load on a single wheel by slightly lifting the wheel with load sensing rods that measure the wheel load. A variety of different alarm signals are used signal to warn a care giver. The device is self-contained, self-secures and removes itself from a variety of different diameter wheels. The device can auto calibration when the wheel is initially lifted and also calibrate when a patient is resting on a bed. The monitoring establishes a threshold load without a patient and with a patient to allow the software to determine when the on an edge of a bed and also when a patient has completely left the bed. Software filtering rejects patient movement to prevent false alarms.

19 Claims, 3 Drawing Sheets

(56) References Cited

U.S. PATENT DOCUMENTS

| | | | |
|---|---|---|---|
| 6,067,019 A * | 5/2000 | Scott | 340/573.4 |
| 6,133,837 A * | 10/2000 | Riley | 340/573.1 |
| 6,239,706 B1 * | 5/2001 | Yoshiike et al. | 340/573.4 |
| 6,380,496 B1 * | 4/2002 | Lohkamp | 177/144 |
| 6,518,520 B2 * | 2/2003 | Jones et al. | 177/144 |
| 7,242,308 B2 * | 7/2007 | Ulrich et al. | 340/573.1 |
| 7,253,366 B2 | 8/2007 | Bhai | |
| 7,437,787 B2 * | 10/2008 | Bhai | 5/613 |
| 7,589,288 B2 * | 9/2009 | Wu et al. | 177/144 |
| 7,656,299 B2 | 2/2010 | Gentry et al. | |
| 7,849,545 B2 | 12/2010 | Flocard et al. | |
| 8,405,510 B2 * | 3/2013 | Shieh et al. | 340/573.1 |
| 2002/0196148 A1 * | 12/2002 | Nunome | 340/573.1 |
| 2003/0090383 A1 * | 5/2003 | Conway | 340/665 |
| 2003/0216670 A1 * | 11/2003 | Beggs | 600/595 |
| 2004/0178910 A1 * | 9/2004 | Egger | 340/556 |
| 2005/0035862 A1 * | 2/2005 | Wildman et al. | 340/573.1 |
| 2005/0200488 A1 | 9/2005 | Riley et al. | |
| 2005/0219059 A1 * | 10/2005 | Ulrich et al. | 340/686.1 |
| 2006/0152358 A1 | 7/2006 | Osterweil | |
| 2007/0132558 A1 * | 6/2007 | Rowe et al. | 340/286.07 |
| 2007/0180620 A1 * | 8/2007 | Bellingroth | 5/618 |
| 2007/0288263 A1 * | 12/2007 | Rodgers | 705/2 |
| 2008/0169931 A1 | 7/2008 | Gentry et al. | |
| 2009/0194751 A1 * | 8/2009 | Schmucker et al. | 254/8 R |
| 2009/0260158 A1 * | 10/2009 | Kazuno et al. | 5/600 |
| 2010/0206136 A1 * | 8/2010 | Cheung | 81/3.2 |
| 2011/0208541 A1 * | 8/2011 | Wilson et al. | 705/3 |
| 2012/0025992 A1 * | 2/2012 | Tallent et al. | 340/573.4 |
| 2012/0277637 A1 * | 11/2012 | Vahdatpour et al. | 600/595 |
| 2012/0323090 A1 * | 12/2012 | Bechtel et al. | 600/306 |
| 2013/0245389 A1 * | 9/2013 | Schultz et al. | 600/301 |
| 2013/0285814 A1 * | 10/2013 | Snodgrass | 340/573.1 |
| 2013/0297350 A1 * | 11/2013 | Gross et al. | 705/3 |
| 2013/0300558 A1 * | 11/2013 | Reeder et al. | 340/501 |
| 2013/0314522 A1 * | 11/2013 | Ravid et al. | 348/77 |
| 2014/0000032 A1 * | 1/2014 | Dixon et al. | 5/611 |
| 2014/0069729 A1 * | 3/2014 | Shih | 177/144 |

* cited by examiner

BED PRE-EXIT PATIENT MONITOR

CROSS REFERENCE TO RELATED APPLICATION

This application claims the benefit of Provisional Application Ser. No. 61/433,754 filed Jan. 18, 2011 the entire contents of which is hereby expressly incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates to improvements in a monitoring system for a hospital bed. More particularly, the present bed pre exit patient monitor is temporally installed onto a wheel of a hospital bed. The load on the wheel is monitored to determine if a patient has moved to an edge of a bed before the patient exits the bed. The device has two arms that straddle a wheel of the bed and the arms move together to lift the wheel off of the ground to begin monitoring the load on the arms.

2. Description of Related Art Including Information Disclosed Under 37 CFR 1.97 and 1.98

The need to monitor the presence of a patient in a hospital bed in important to eliminate harm to a patient that is not capable of supporting their weight. In some cases the monitor is one or more switch(es) that identify when a patient has moved, rolled, or left a bed completely. Monitoring the bed for the absence of a patient does not stop a patient before they leave the bed. Other systems use load cells that are integrated into the wheel posts. These systems require that each hospital bed have the load cells thereby increasing the cost of the bed. Several products and patents have been issued that try to solve this problem. Exemplary examples of patents covering these products are disclosed herein.

U.S. Pat. No. 2,818,477 issued Dec. 31, 1957 to P. J. Gollhofer, U.S. Pat. No. 3,961,201 issued Jun. 1, 1976 to Morris Rosenthal and U.S. Pat. No. 4,539,560 issued Sep. 3, 1985 to David Fleck et al., disclose a bed patient monitoring system that uses mechanical switches to determine when a patient is not in a bed. While these patents disclose a system to determine if a patient is not in the bed the system only detects when the person is not present. It does not determine or discriminate when a person is on the edge of a bed before they get out of the bed. These patents also must be placed within the bed before the patient is placed into the bed.

U.S. Pat. No. 4,633,237 issued Dec. 20, 1986 to Kenneth Tacknott et al., U.S. Pat. No. 5,844,488 issued Dec. 1, 1998 to Jeff Musick and U.S. Pat. No. 7,656,299 on Feb. 2, 2010 to Jason Gentry et al., disclose a bed monitoring system that uses an array of sensors that are placed under a patient to determine if a patient moves or is absent from a bed. These patents disclose a system to determine if a patient moves or is not in the bed the system does not detect when a person has moved to the edge of a bed before they attempt to leave the bed. These patents also must be placed within the bed before the patient is placed into the bed.

U.S. Pat. No. 5,823,278 issued Oct. 20, 1998 and U.S. Pat. No. 5,832,221 issued Nov. 3, 1998 both to Randy Geringer and U.S. Pat. No. 7,437,787 issued Oct. 21, 2008 to Alex Bhai disclose a bed monitoring or patient weighing system using strain gauges that are placed integrated into the legs of the bed. These patents require that the hospital bed is manufactured with the integrated strain gauges built into the legs or posts of the bed. The load sensors can't be removed from the bed and moved to other beds. The monitoring system must integrate the signal from sensors placed on numerous legs to determine what the patient is doing.

What is needed is a patient monitoring system that can be temporally placed onto a wheel of a hospital bed to monitor when a patient is preparing to leave a bed. The proposed application provided the solution with a device that can be slid onto a wheel and activated to slightly raise the wheel to determine if a patient is about to exit a bed.

BRIEF SUMMARY OF THE INVENTION

It is an object of the bed pre exit patient monitor to monitor the load on the bed to filter out patient movement and determine when a patient has moved to an edge of the bed prior to the patient leaving the bed. When a patient slides to either edge of the bed they load on a single wheel will significantly increase or decrease. The monitoring of the bed and establishing the load without a patient and with a patient allows the software to determine when the on an edge of a bed. This will further include patient motion filtering movement rejection to prevent false alarms.

It is an object of the bed pre exit patient monitor to be motorized to automatically lift and lower a wheel. The lifting mechanism includes a pair of rods that are attached to strain gauges to monitor the load on the wheel. The rods move together and apart to squeeze the wheel and slightly lift the wheel off of the ground. Once the monitoring is no longer required the rods move apart to release the wheel for use on another bed. The pair of rods can accommodate a variety of different diameter wheels. The device can determine when the wheel is slightly lifted off of the ground.

It is an object of the bed pre exit patient monitor to include an alarm to notify a care giver that a patient is take action before the patient stands off of the bed. The alarm can take a variety of different types including but not limited to a wireless signal, an audible alarm, a mechanical relay, switch closure or a visible signal. The alarm may have variable tones or signals based upon the estimated status of the patient on the bed. The alarm can be reset programmed and adjustable. The alarm may also include a low battery indicator to identify when the device needs to be charged, batteries replace or the device replaced with a charged device.

It is another object of the bed pre exit patient monitor to be self-contained where the bed pre exit patient monitor can be easily moved from bed to bed. The bed pre exit patient monitor includes a power supply, motorized rods to lift the wheel, software intelligence and control to operate the device.

It is another object of the bed pre exit patient monitor to determine a patient's weight. Use of multiple devices can collectively determine the weight of a patient by summing the load on all of the wheels.

It is still another object of the bed pre exit patient monitor to auto calibrate. The auto calibration can zero the device when the wheel is initially lifted and also calibrate when a patient is resting on a bed. The calibration can include adjustment for zero offset and gain.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

DETAILED DESCRIPTION OF THE INVENTION

Figure 1:
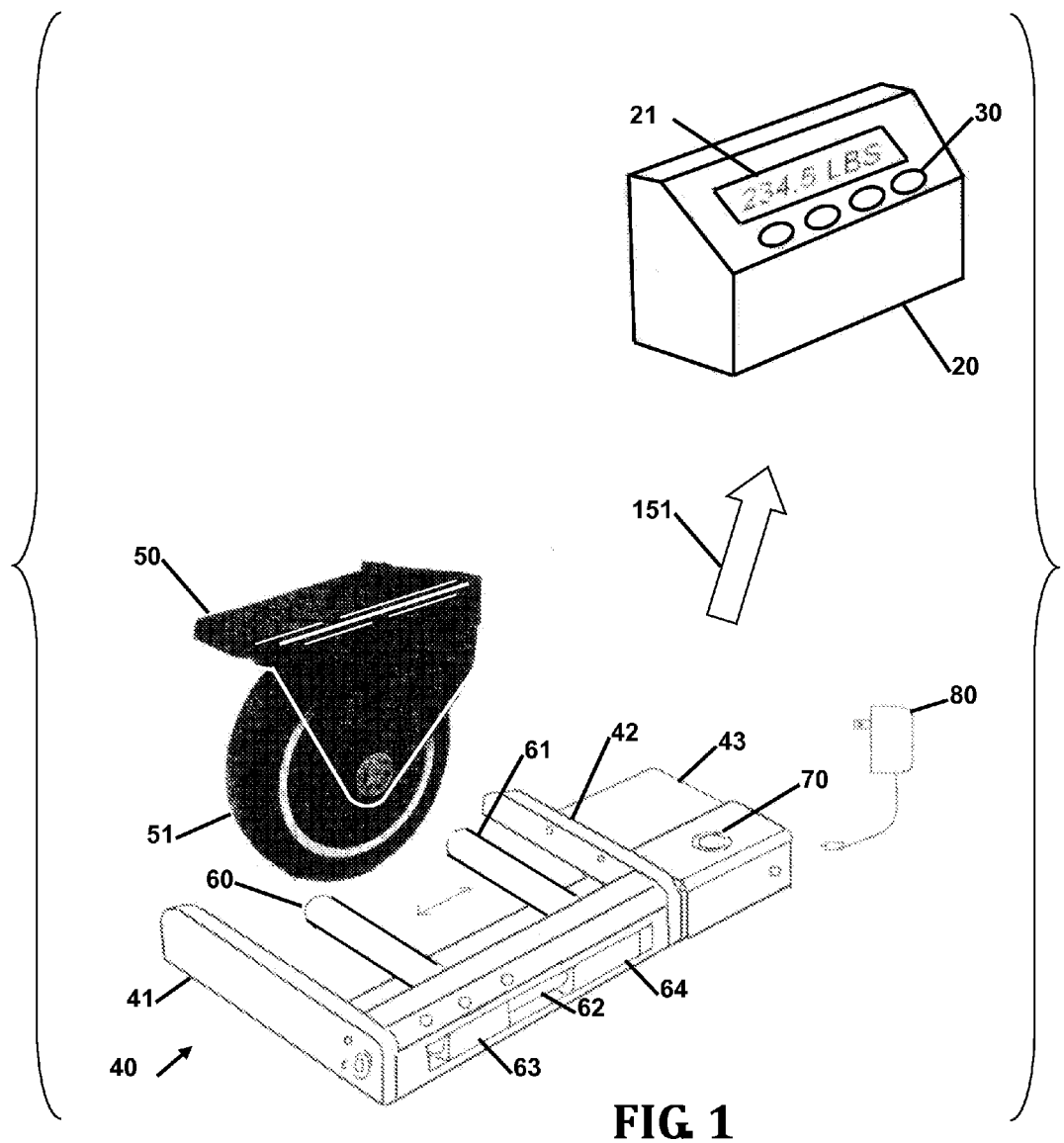
FIG. 1 shows an isometric view of a bed pre exit patient monitor in a preferred embodiment showing wheel monitor and a separate display unit.

FIG. 1 shows an isometric view of a bed pre exit patient monitor in a preferred embodiment showing wheel monitor and a separate display unit. In this preferred embodiment a separate display unit 20 is shown, but it is also contemplated that the display 21 and control buttons can be integrated into the base unit 40. The separate display unit 20 is preferably separate so it can be located distal from the bed that is being monitored. The display unit 20 shows a digital readout 21 with the estimated weight of the person in the hospital bed. The display unit is linked to the base unit with a wired or wireless communication link 151. The base unit is preferably made with aluminum or stainless steel housing and frame so the components can be cleaned if necessary to reduce cross contamination from one patient to another.

The base unit 40 includes a pair of movable rods 60. In operation the base unit is slid onto the wheel 51 of the support structure 50 of a hospital bed. A pair of support arms 41 and 42 help to initially center the wheel 51 between the two rods 60 and 61. Initially the wheel 51 sits on the ground. When the base unit is activated with a start switch 70 or button that is located on the base unit 40 or on the display unit 20, one or both of the movable rods 60, 61 will be driven together with a motor (not shown) within the enclosure 43. A single or dual threaded screw 62 allows either one rod to move towards the other or both rods to move together as they are being driven with nuts 63 and 64. The bottom of the base unit is smooth or covered with a low friction material to allow the base unit to slide and center itself under the wheel 51.

As the two rods make contact with the outer sides of the wheel 51 they will squeeze the wheel together and lift the wheel 51 slightly off of the ground until the entire weight from the wheel is resting on the base unit 40. Because the size of the wheel 51 on a hospital bed is not known the loading rods 60 and 61 are adjustable to accommodate wheels from small diameter to extremely large diameters. Once the base unit is lifts the wheel 51 off of the ground the internal software calibrates the normal load on the rod(s) 60 and 61. While one or two rods may have strain gauges or load cells attached to the rods, it is contemplated that at least one rod will have load sensing capability to determine movement of a patient on the bed. While only one base unit is shown it is contemplated that multiple base units can be used and can communicate to a single or multiple display units 20. When multiple units are used the accuracy of measurement from four separate units can provide highly accurate measurement of the weight of a patient on the bed.

When monitoring of the bed is no longer required the start/stop button 70 can be pressed or one of the buttons 30 on the display unit can be pressed and the rod(s) 60 and 61 are separated to release the wheel 51 and allow the base unit to be moved for storage or use with other beds. It is further contemplated that the base unit and or the display unit to be self-contained and operates off of battery power. A wall charger can charge the unit(s) or can be used for an extended period.

Figure 2:
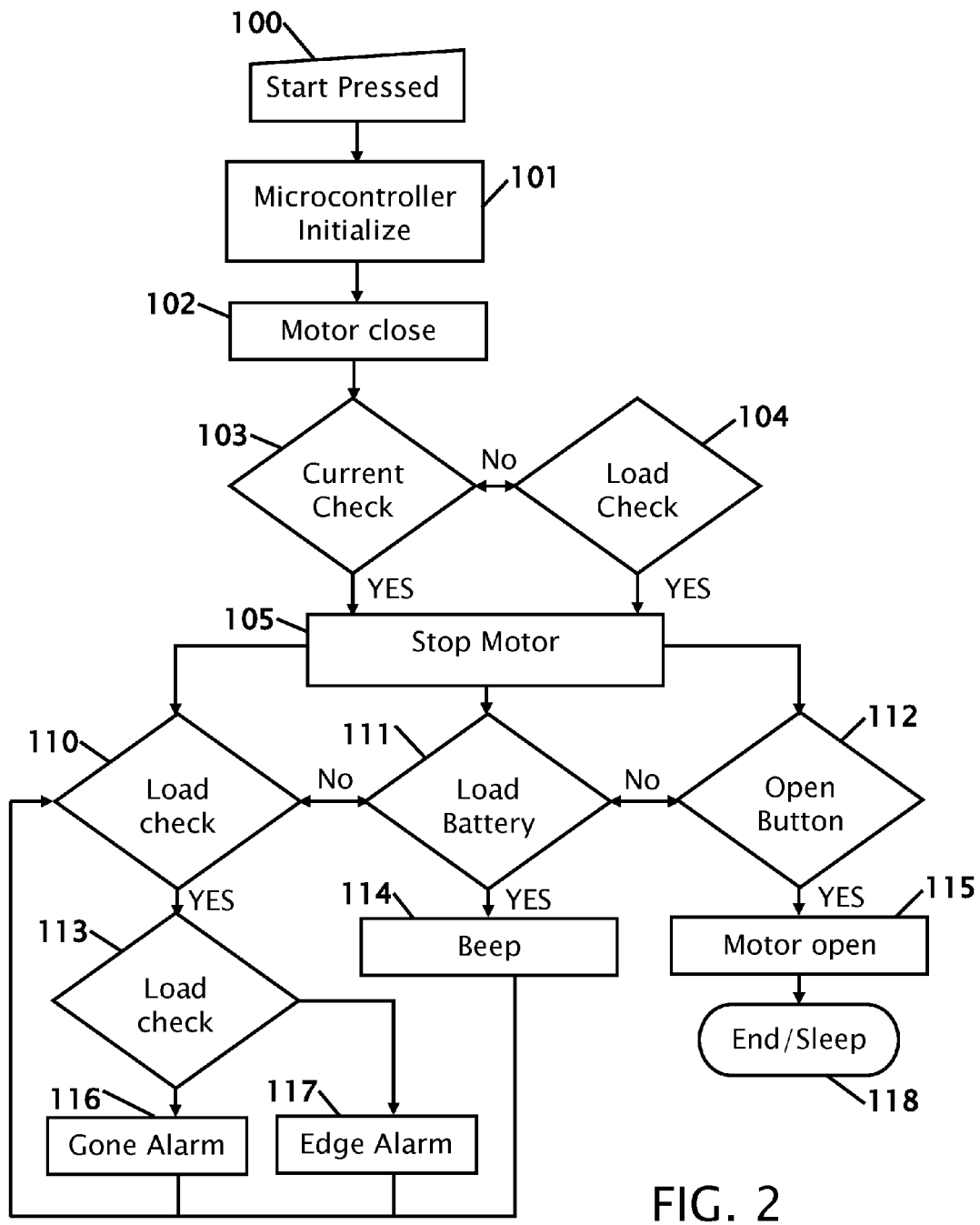
FIG. 2 shows a simplified flow diagram of the software operation.

FIG. 2 shows a simplified flow diagram of the software operation. Pressing the start button 100 will initialize the device and start the microcontroller 101. After a brief start-up sequence the base unit will communicate to an internal or external display unit to indicate that internal checks are passed. Some functions of the start-up sequence include but are not limited to calibration, detection of internal or external power and establishing communication with other related devices. The microcontroller will engage solid state or mechanical relays to the drive system to move the rod or rods 60 and 61 as shown in FIG. 2. The motor closes the distance between the rods 60 and 61 to pinch a wheel. The microcontroller can sense the power or current 103 being used by the drive motor and or the load 104 on the rods 60 and 61 to determine when contact has been made with the wheel 51 and when the wheel has been lifted off the ground. Because the diameter of the wheel 51 may not be initially known or may be variable the device must autonomously determine when the wheel is slightly off of the ground to limit tipping or rocking from the remaining wheels of the bed.

Once the wheel is slightly lifted off of the ground the motor will be turned off or stopped 105. At this point an initial load for the patient on the bed is established and a load check 110 in continuously monitored. Multiple devices can be secured to each of the wheels 51 to provide a total summed load or weigh for the entire bed with and without a patient. The separate data from each device can be summed and displayed. In addition to monitoring the load the battery level 111 and the button(s) 112 are monitored to determine if the device will be de-activated or opened.

A single monitoring device can be used to provide the detection of a patient that is on the edge of a bed because if the patient moves to the side where the monitor is located the load will significantly increase whereas when the patient moves to the far edge away from the monitor the recorded load will decrease. The load check 113 has at least two thresholds to determine if a patient is on the edge of a bed or completely off of the bed. Each threshold can have a different alarm based upon the measured load such as an edge alarm 117 and a gone alarm 116.

The load check software monitors the load of the user over an extended period of time to filter out movements of the patient such as a patient rolling, shifting or a visitor resting on an edge of the bed.

When low voltage or a low voltage threshold is detected the device will emit a low voltage chirp 114 or beep and or send a notice to the display. The low voltage warning can be cleared by connecting a charger or simply by replacing the batteries. It is contemplated that the microcontroller has internal non-volatile memory where old batteries can be removed and a charged batteries can be installed without requiring the device to be re-calibrated.

If the open button is depressed 112 the motor will be energized and the rod(s) 60 and 61 will open 115 to release the wheel 51 and enter into a low power sleep mode. It is contemplated that the current of the motor can be monitored or an end of travel limit switch can be used to identify when the rod(s) have been completely opened.

Figure 3:
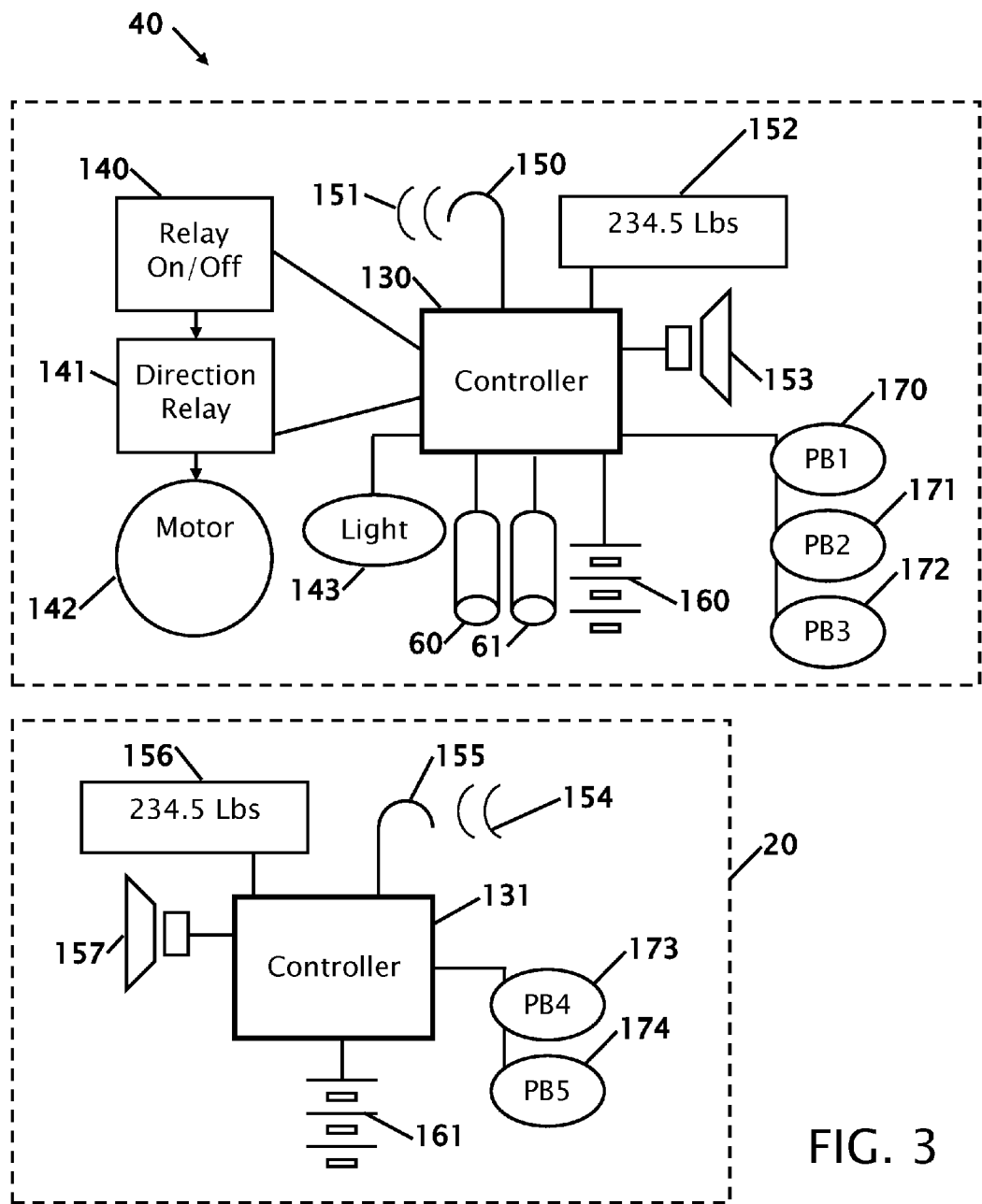
FIG. 3 shows a block diagram of the components.

FIG. 3 shows a block diagram of the components. In the main unit 40 a micro controller 130 is the central part of the device and is powered by batteries 160 and or an external transformer 80 as shown in FIG. 1. The controller 130 is connected to an on/off power relay 140 and a directional relay 141 that controls the drive motor 142. The rods 60 and 61 are connected to strain gauges with amplifiers that are measured by the controller 130. One or more switches 170, 171 and 172 provide control for opening and closing the base unit and can also function to set or silence the alarm 153 and provide user input for additional calibration if required. A display 152 may be included to provide local user feedback of the status of the device and the patient being monitored. An indicator light may also be included to provide a visible notice without using an audible signal 153 that could disturb a sleeping patient such as when the batteries are low. A wireless link 151 or signal from a transmitter 150 can send a wireless signal to the receiver unit 20. Using a variety of frequencies or protocols including but not limited to RF, IR and Bluetooth.

The receive unit 20 also includes a controller 131 that can receive a signal 154 from the base unit. An antenna 155 can receive the signal and display the monitored load 146, weight or other information as well as provide an audible alarm 157 if the care giver needs to immediately check on the status of the patient. One or more buttons 173 and 174 can control the base unit from a distance to silence an alarm or turn off the base unit. The receive unit 20 can also powered by batteries 161 and or with an external transformer (not shown).

Thus, specific embodiments of a bed pre exit patient monitor have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. A bed pre-exit patient monitor for determining when a patient has moved to an edge of a bed prior to the patient leaving the bed by measuring a load on a single wheel of the bed by slightly lifting said single wheel with two parallel members to measure the load of said single wheel, the bed pre-exit patient monitor comprising:
a two-direction drive motor secured to at least one of the two parallel members on a stationary base of the bed pre-exit patient monitor;
at least one of said two parallel members secured to a load sensor; wherein the at least one of said two parallel members is moved by said two-direction drive motor toward to the other one of the two parallel members to at least partially lift said single wheel of the bed placed between said two parallel members to allow said load sensor to determine the load on said load sensor;
said at least partially lifting is determined by said load sensor;
a controller configured to determine a bed empty load and a bed full load using said load sensor, wherein the bed empty load represents the bed without the patient and the bed full load represents the bed with the patient; and
said load from said single wheel is measured to determine when the patient on said bed is on an edge of said bed by determining a temporal increase or decrease on said single wheel transition between said bed empty load and said bed full load;
wherein the bed-pre-exit patient monitor further includes at least one start button or switch that operates said two-direction drive motor to move the at least one of said two parallel members toward to the other one of said two parallel members until said load sensor determines when said single wheel is supported on said parallel members and then stops the operation of said two-direction drive motor.

2. The bed pre-exit patient monitor according to claim 1 that further includes an alarm to indicate when the patient is on the edge of the bed or completely out of the bed.

3. The bed pre-exit patient monitor according to claim 2 wherein said alarm is an audible alarm.

4. The bed pre-exit patient monitor according to claim 2 wherein said alarm is a visible alarm.

5. The bed pre-exit patient monitor according to claim 2 wherein said alarm sends a wired signal to a receiver.

6. The bed pre-exit patient monitor according to claim 2 wherein said alarm sends a wireless signal to a receiver.

7. The bed pre-exit patient monitor according to claim 6 wherein said wireless signal is RF, IR or Bluetooth.

8. The bed pre-exit patient monitor according to claim 1 wherein said two direction drive motor releases said two parallel members from said single wheel based at least partially upon a reading from said load sensor.

9. The bed pre-exit patient monitor according to claim 1 wherein said two direction drive motor moves both of said parallel members.

10. The bed pre-exit patient monitor according to claim 1 wherein said load sensor determines when the patient is on an edge of said bed by an increase of load on said load sensor on said single wheel.

11. The bed pre-exit patient monitor according to claim 1 wherein said load sensor determines when the patient is on an edge of said bed by a decrease of load on said load sensor on said single wheel.

12. The bed pre-exit patient monitor according to claim 1 wherein said load sensor can be calibrated to determine the load on said at least two parallel members.

13. The bed pre-exit patient monitor according to claim 12 wherein a weight of said bed can be tarred out.

14. The bed pre-exit patient monitor according to claim 1 that further includes at least one display.

15. The bed pre-exit patient monitor according to claim 14 wherein said display is at least one digital readout or at least one LED.

16. The bed pre-exit patient monitor according to claim 1 wherein said bed pre-exit patient monitor is battery and or externally powered.

17. The bed pre-exit patient monitor according to claim 1 that further includes a low battery or power sensor and a low battery or power notification mechanism.

18. The bed pre-exit patient monitor according to claim 1 that further includes a digital or electrical filter to reduce false errors that are causes by the patient rolling or turning in said bed.

19. The bed pre-exit patient monitor according to claim 1 wherein said two-direction drive motor is energized by a mechanical or solid state relay.

* * * * *